(12) United States Patent
Parikh et al.

(10) Patent No.: US 7,985,419 B1
(45) Date of Patent: Jul. 26, 2011

(54) DIVISIBLE TABLET AND ASSOCIATED METHODS

(75) Inventors: Nilesh H. Parikh, Irvine, CA (US); William Crawford Hite, Winchester, CA (US); Bhavesh R. Patel, Mission Viejo, CA (US)

(73) Assignee: Watson Laboratories, Inc., Salt Lake City, UT (US)

( * ) Notice: Subject to any disclaimer, the term of this patent is extended or adjusted under 35 U.S.C. 154(b) by 972 days.

(21) Appl. No.: 11/644,985

(22) Filed: Dec. 22, 2006

(51) Int. Cl.
*A61K 9/20* (2006.01)
*A61K 9/44* (2006.01)

(52) U.S. Cl. .................. 424/464; 424/465; 424/467

(58) Field of Classification Search ............ None
See application file for complete search history.

(56) References Cited

U.S. PATENT DOCUMENTS

| | | |
|---|---|---|
| 2,052,376 A | 8/1936 | Zellers |
| D201,497 S | 6/1965 | Ninger |
| 3,336,200 A | 8/1967 | Krause et al. |
| 3,723,614 A | 3/1973 | Langauer |
| D229,049 S | 11/1973 | Roberts |
| RE29,077 E | 12/1976 | Geller |
| 4,215,104 A | 7/1980 | Ullman et al. |
| 4,258,027 A | 3/1981 | Ullman |
| 4,353,887 A | 10/1982 | Hess et al. |
| 4,493,822 A | 1/1985 | Tovey |
| 4,503,031 A | 3/1985 | Glassman |
| 4,683,131 A | 7/1987 | Zierenberg et al. |
| 4,735,805 A | 4/1988 | Ni et al. |
| 4,824,677 A | 4/1989 | Shah et al. |
| D310,579 S | 9/1990 | Ni et al. |
| 5,009,896 A | 4/1991 | Becker |
| 5,061,494 A | 10/1991 | Ni et al. |
| D323,388 S | 1/1992 | Becker |
| 5,520,929 A | 5/1996 | Makino et al. |
| D384,410 S | 9/1997 | Hessom et al. |
| 5,756,124 A | 5/1998 | Patel et al. |
| D424,686 S | 5/2000 | Lam |
| D440,650 S | 4/2001 | Hite et al. |
| 6,342,247 B1 | 1/2002 | Miyabe et al. |
| 6,342,248 B1 * | 1/2002 | Miyabe et al. ............... 424/467 |
| 6,365,183 B1 | 4/2002 | Edgren et al. |
| 6,692,765 B1 | 2/2004 | Spengler |
| 2005/0181070 A1 * | 8/2005 | Gadde et al. ................. 424/722 |
| 2006/0193909 A1 | 8/2006 | Stawski et al. |

FOREIGN PATENT DOCUMENTS

| | | | |
|---|---|---|---|
| EP | 0 207 888 | | 1/1987 |
| EP | 1568362 | * | 8/2005 |

OTHER PUBLICATIONS

Reynolds, 1990. Remington's Pharmaceutical Sciences. Chapter 89. Oral solid dosage forms, pp. 1633-1665.* van santen, et al, 2002. Breaking of scored tablets: A review. European journal of pharmaceutics and Biopharmaceutics, vol. 53:139-145.*

* cited by examiner

*Primary Examiner* — Shanon A Foley
(74) *Attorney, Agent, or Firm* — Florek & Endres PLLC

(57) ABSTRACT

A divisible pharmaceutical tablet comprises an upper portion and a lower portion, the upper portion including at least one upper convex surface bordering at least one dividing notch. A ridgeline is formed between the at least one dividing notch and the at least one upper convex surface. The upper convex surface includes an apex defined at a location along the ridgeline.

49 Claims, 3 Drawing Sheets

DIVISIBLE TABLET AND ASSOCIATED METHODS

FIELD OF THE INVENTION

The present invention relates generally to tablets for use in delivering pharmaceutical compositions. In particular, the present invention relates to tablets that can be easily divided to provide sub-dosages of the pharmaceutical composition, and methods associated therewith.

BACKGROUND OF THE INVENTION

Divisible pharmaceutical tablets have been known for some time. Such tablets generally allow a pharmaceutical composition to be provided to patients in a measured, predetermined dose. Should the patient be prescribed to, or otherwise desire to, sub-divide the predetermined dose into one or more smaller doses, she can break or fracture the divisible tablet along one or more score lines to form individual fragments or sub-portions of the tablet. Each sub-portion generally includes a fractional amount of pharmaceutical; with tablets often being divisible into equal portions, such as half portions, third portions, quarter portions, etc.

Many competing design goals exist which are relevant to divisible tablets. For example, such tablets should be relatively easy to divide so that patients (and/or medical professionals) can divide the tablets at will. However, such tablets should not be overly frangible; otherwise they may be unintentionally broken during packaging, storage or transport. Also, such tablets (and fractional portions of such tablets), should not be easily broken in general, otherwise the desired pharmaceutical content in the tablet (or the fractional portions of the tablet) may be altered due to crumbling, flaking, etc. In addition, such tablets should be consistently divisible into substantially constant, predictable fractional portions, so that any one of the fractional portions of the tablet does not contain a significantly greater or lesser amount of the pharmaceutical active ingredient than it is intended to contain. Further, tablets and capsules in general should be configured to facilitate relatively effortless deglutition by patients.

SUMMARY OF THE INVENTION

Accordingly, the present invention provides a divisible pharmaceutical tablet that is not subject to premature breakage and that can be relatively easily divided into sub-portions, with the sub-portions containing consistently accurate amounts of pharmaceuticals.

In accordance with one embodiment, a divisible pharmaceutical tablet is provided, including an upper portion and a lower portion. The upper portion can include at least one upper convex surface bordering at least one dividing notch. A ridgeline can be formed between the at least one dividing notch and the at least one upper convex surface. The upper convex surface can have an apex defined at a location along the ridgeline.

In accordance with another aspect of the invention, a divisible pharmaceutical tablet is provided, including an upper portion and a lower portion, the lower portion including at least one lower convex surface. The upper portion can include a plurality of upper convex surfaces bordered by at least one dividing notch. A width of the at least one dividing notch can taper from a largest width adjacent a center of the notch to a narrowest width adjacent an edge of the tablet.

In accordance with another aspect of the invention, a divisible pharmaceutical tablet is provided, including an upper portion and a lower portion, the lower portion having a lower, substantially uninterrupted convex surface. The upper portion can include a plurality of upper convex surfaces with a pair of dividing notches bordering at least some of the upper convex surfaces. The dividing notches can extend across the upper portion in different directions of extension.

In accordance with another aspect of the invention, a divisible pharmaceutical tablet is provided, including an upper portion and a lower portion. The upper portion can include a plurality of upper convex surfaces with at least one dividing notch separating the upper convex surfaces. Each of the convex surfaces can have a curvature that, when extrapolated across the at least one dividing notch, converges into a shape substantially the same as a shape of the lower portion.

There has thus been outlined, rather broadly, relatively important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

DETAILED DESCRIPTION

Figure 1:
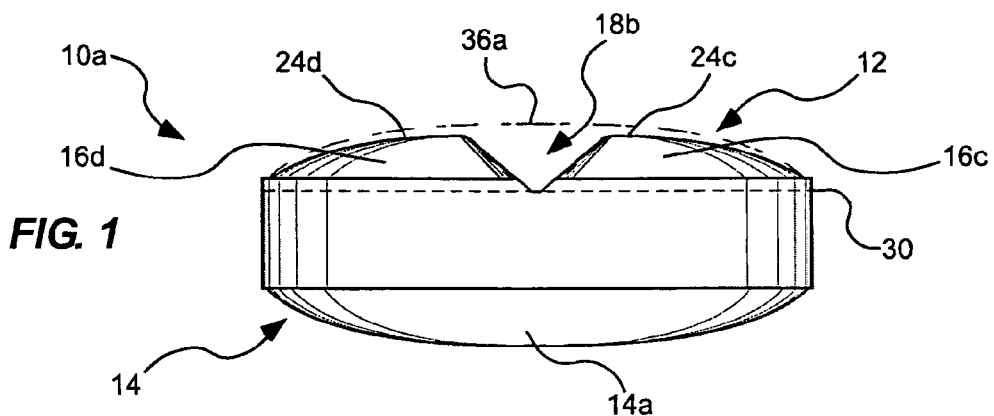
FIG. 1 is a side view of a divisible tablet in accordance with an embodiment of the present invention.

Before the present invention is disclosed and described, it is to be understood that this invention is not limited to the particular structures, process steps, or materials disclosed herein, but is extended to equivalents thereof as would be recognized by those of ordinarily skilled in the relevant arts. It should also be understood that terminology employed herein is used for the purpose of describing particular embodiments only and is not intended to be limiting.

It must be noted that, as used in this specification and the appended claims, the singular forms "a" and "the" include plural referents, unless the context clearly dictates otherwise. Thus, for example, reference to an "apex" can include one or more of such apexes.

Definitions

In describing and claiming the present invention, the following terminology will be used in accordance with the definitions set forth below.

As used herein, the term "convex" is used to refer to the state of a surface or a line as generally being curved or rounded outwardly. It is to be understood that, when the term convex is used herein to describe a property of a surface, the surface being referenced is convex in a three-dimensional space. That is, portions of a convex surface slope away from and downward relative to an apex of the surface, from all directions from the apex (although different segments of the surface may slope to a greater or lesser degree than other segments). As an example, the outer surface of a typical optical contact lens would be considered a convex surface, as that term is used herein.

An example of a geometrical shape that would not meet the definition of a convex surface, as that term is used herein, is a conventional cylinder. As the surface of a conventional cylinder diverges from an apex in only two opposing directions from the apex (e.g., the slope of the wall doesn't change in one direction of travel from the apex), it does not include a convex surface, as that term is used herein.

As used herein, the term "apex" is to be understood to refer to a portion of a curvature (whether or not the curvature is formed by a line or a surface) from which adjacent portions of the curvature slope away. In other words, the apex forms the "highest" portion of a curvature, the portion above which no other portion of the curvature rises. It is to be understood that, as used herein, the term apex may refer to a single point in space, or may refer to a collection of generally co-planar points in space. Thus, a small, flat section of a surface can comprise an apex, as can a sharply peaked portion (e.g., a single point) of the surface.

As used herein, the term "pharmaceutical" or "pharmaceutical composition" may be used interchangeably to refer to an agent or substance that has measurable specified or selected physiologic activity when administered to a subject in a significant or effective amount. These terms of art are well-known in the pharmaceutical and medicinal arts.

As used herein, the term "substantially" refers to the complete or nearly complete extent or degree of an action, characteristic, property, state, structure, item, or result. For example, an object that is "substantially" enclosed is an object that is either completely enclosed or nearly completely enclosed. The exact allowable degree of deviation from absolute completeness may in some cases depend on the specific context. However, generally speaking the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

Distances, angles, forces, weights, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 inch to about 5 inches" should be interpreted to include not only the explicitly recited values of about 1 inch to about 5 inches, but also include individual values and sub-ranges within the indicated range. This same principle applies to ranges reciting only one numerical value and should apply regardless of the breadth of the range or the characteristics being described.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Invention

As illustrated generally in the attached figures, in one aspect of the present invention a divisible pharmaceutical tablet 10a, 10b is provided. The tablet can be used to provide various pharmaceutical compositions to patients and can be formed from a variety of materials known to those of ordinary skill in the art. The type of pharmaceutical composition provided in the tablet can vary widely, from medicaments or drugs available only under a doctor's prescription, to over-the-counter compositions.

In one aspect of the invention, the tablet is used to provide a therapeutic dosage of levetiracetam, a drug commonly used to treat various conditions, including epilepsy. In one aspect of the invention, the tablet can be used to provide a therapeutic dosage of escitalopram. In another aspect, the tablet can be used to provide a therapeutic dosage of oxcarbazepine. The tablets of the present invention can include, in addition to the pharmaceutical agent, various fillers and additives including, without limitation, flavoring additives, coatings, carriers, lubricants, binders, fillers, etc. The tablet can be formed in a variety of known manners, including compression molding methods and similar processes.

Figure 2:
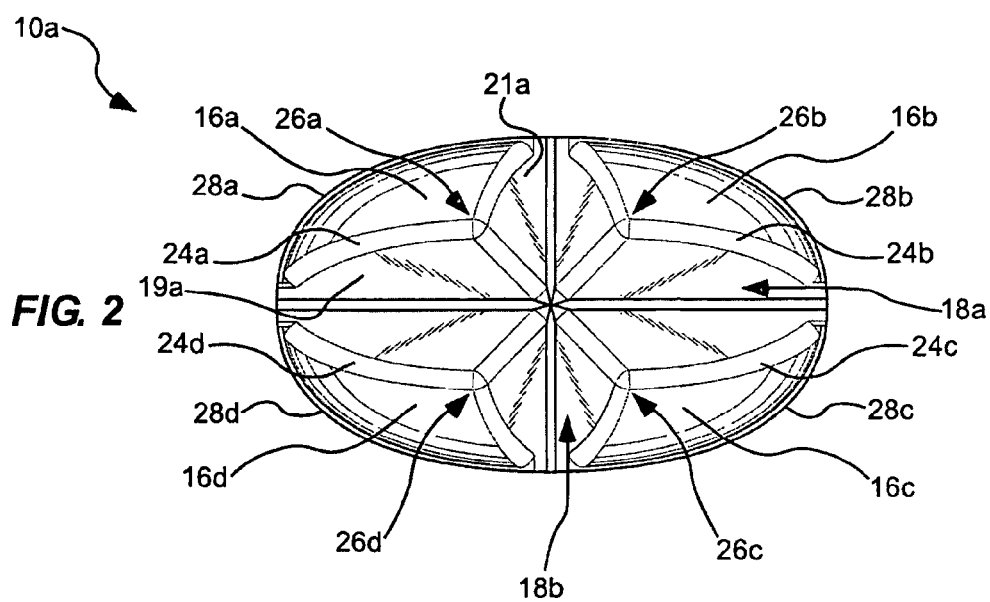
FIG. 2 is a top view of the tablet of FIG. 1.
Figure 3:
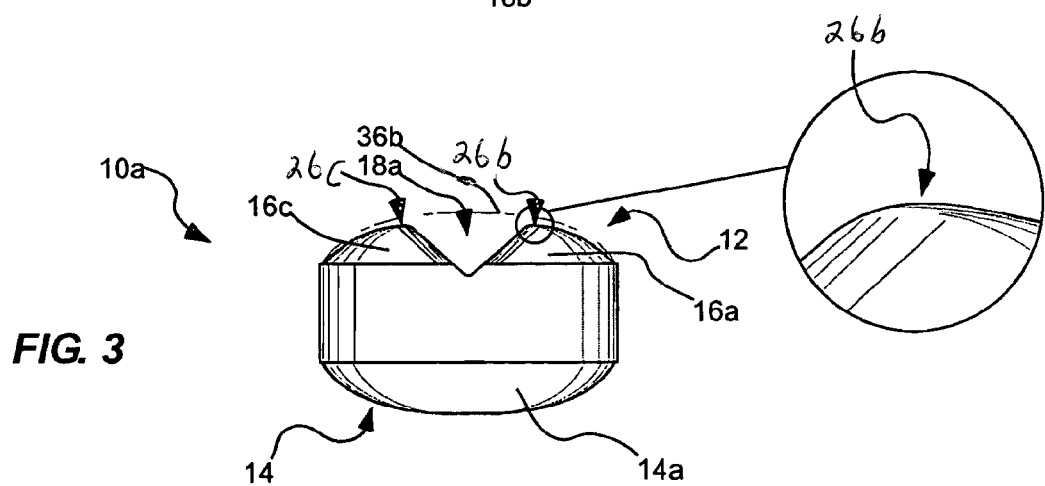
FIG. 3 is an end view of the tablet of FIG. 1.

As shown in detail in FIGS. 1-3, in one aspect of the invention, a divisible pharmaceutical tablet 10a is provided that can include an upper portion 12 and a lower portion 14. Referring primarily to FIG. 2, the upper portion can include at least one upper convex surface (four of which are shown at 16a, 16b, 16c and 16d) that borders at least one dividing notch (two of which are shown at 18a and 18b). A ridgeline 24a, 24b, 24c or 24d can be formed between the at least one dividing notch and the at least one upper convex surface. The upper convex surface can have an apex 26a, 26b, 26c and 26d defined at a location along the ridgeline.

While not required in all embodiments, in the aspect of the invention illustrated in FIGS. 1-3, the tablet 10a includes a pair of dividing notches 18a and 18b. The pair of dividing notches can extend across the upper portion of the tablet in different directions of extension. For example, as best shown in FIG. 2, the dividing notch 18a extends longitudinally across the upper portion while the dividing notch 18b extends laterally across the upper portion. The tablet 10a is thus divisible into four segments of substantially equal volume, represented by segments 28a, 28b, 28c and 28d.

Thus, in this embodiment of the invention, the tablet 10a can be split into at least two fractional portions, one of which includes segment 28a and 28b, and one of which includes segments 28c and 28d. Alternately, the tablet 10a can be split into two fractional portions, one of which includes segment 28a and 28d, and one of which includes segments 28b and 28c. Also, each of the half-segments discussed immediately above can also be split into two fractions, such that four total segments can be created from the single tablet 10a.

In this manner, the present invention allows a consumer to divide the tablet into two or more sub-portions to allow the consumer to create incremental, fractional dosages for use by the consumer. Depending upon the composition of the tablet, one or more of the fractional dosages can be used by the consumer at the time of splitting, and the remaining portions can be saved for use at a later time.

While the examples shown in the accompanying figures include a tablet divisible into four segments of substantially equal volume, it is to be understood that tablets of the present invention can be divisible into a number of different fractional pieces, including, without limitation, 2 fractional pieces, 3 pieces, 5, 6, 7, 8, etc.

In addition, while the segments shown are of substantially equal volume, it is to be understood that tablets of the present invention can be divisible into multiple segments that are not necessarily equal in volume. In one example (not shown), a tablet can be provided that can be divisible into three segments, with one segment having a volume approximately equal to the combined volume of the remaining two segments.

Regardless of the number, size, shape or volume of the segments into which the present tablet can be divided, division thereof produces segments that consistently provide a desired dosage of the pharmaceutical agent being administered. In one aspect of the invention, the dosage uniformity provided by the individual segments can be dosage units of within about 85% to about 115% of the labeled amount indicated for each segment in accordance with the USP-NF dosage uniformity guidelines. In another aspect, the dosage uniformity provided may be within about 80% to about 120%, inclusive of sub-ranges within this span. In yet another aspect, the dosage uniformity may be from about 90% to about 110%. In a further aspect, the dosage uniformity may be from about 95% to about 105%. In another aspect, the dosage uniformity may be about 100%.

While the embodiments illustrated in the figures include dividing notches 18a, 18b that extend longitudinally and laterally across the tablet, in one embodiment of the invention (not shown in the present figures), one or more dividing notches can extend across the tablet at an oblique angle relative to a longitudinal axis of the tablet. For example, one or more dividing notches can extend across the tablet at an angle of about 45 degrees relative to the longitudinal axis of the tablet. In another embodiment, one or more dividing notches can extend across the tablet at an angle of about 30 degrees relative to the longitudinal axis of the tablet.

As shown in the figures, in one embodiment of the invention, two or more dividing notches can be formed in the tablet in an intersecting relationship. In some embodiments, however (not shown), two or more dividing notches can be formed in the tablet (or other dosage form) in a generally parallel relationship. For example, a series of three generally parallel dividing notches can be formed in the tablet at desired intervals to facilitate division of the tablet into three segments.

The dividing notches 18a, 18b can create a weakness in the tablet sufficient to facilitate division of the tablet by the manual application of force to the tablet. When a consumer wishes to divide the tablet, she can apply a bending force to the tablet by, for example, applying force with her fingers and/or thumbs to opposing sides of the tablet adjacent the dividing notches 18a or 18b, and thereby "break" the tablet into fragments.

In some embodiments of the invention the apexes 26a, 26b, 26c and 26d can be utilized, along with a relatively hard surface, to fracture or divide the tablet. In an exemplary application, the tablet can be placed on the hard surface with the apexes in contact with the hard surface and with the lower portion 14 directed upwardly from the surface. A downward force can then be applied by the user to the lower portion, causing the apexes to tend to move outwardly (or inwardly, depending upon the configuration of the tablet) from one another. As the apexes are forced outwardly, a tensile load is applied to the root or base of the dividing notches, resulting in the tablet becoming fractured into two or more pieces. By orienting the apexes 26a-26d as shown in the figures, relative to the remaining portions of the tablet 10a, accurate division of the tablets can be obtained on a consistent, repeatable basis.

In one embodiment of the invention, one or more of the segments 28a, 28b, 28c and/or 28d can have an upper half that includes three sides of differing geometry. For example, in the embodiment illustrated in FIG. 2, segment 28a includes three sides of differing geometry—two notch sides 19a and 21a that are formed as part of the dividing notches 18a and 18b, respectively, and one side that is the upper convex surface 16a. In one aspect of the invention, the notch sides 19a and 21a include a substantially flat, planar surface that is angled upwardly and outwardly from the root or valley (e.g., 30 in FIG. 1) of the notches. In other embodiments, the notch sides can include a curvature, for example a concave or convex curvature (not shown in the present figures) that extends in an arc from the root or valley to the ridgelines. Thus, in one aspect of the invention, the notch sides can be cupped inwardly, which can aid, in some applications, a user's ability to engage the notch sides and apply force to divide the tablet into segments.

As shown in the detail view of FIG. 3, apex 26b can include a substantially rounded edge. The substantially rounded edge and the convex surface can increase the ease of deglutition of the segment 28a by a patient or other end user. While the curvature of the apexes can vary, in one embodiment the apexes include a radius of curvature on the order of about 0.03 inches, with an overall length of the tablet being about 0.8 inches and an overall width of the tablet being about 0.48 inches.

To increase and/or maximize a force applied to a base or root of each of the dividing notches by the application of force by a consumer, a geometry or configuration of one or more of the dividing notches can be varied along a width or a length of the tablet. In one aspect of the invention, one or both of the dividing notches 18a, 18b can include a varying width, with a greatest width formed adjacent a center of the dividing notch. This feature of the invention is illustrated in FIG. 2, where it can be seen that dividing notch 18a includes a width (in this case measured between the ridgelines 24a and 24d or between the ridgelines 24b and 24c), that varies from a maximum near the center of the tablet to a minimum near ends of the tablet. Similarly, the width of the laterally extending dividing notch 18b varies from a maximum near a center of the tablet to a minimum near edges of the tablet.

In one aspect of the invention, one or more of the dividing notches can include a varying depth. As illustrated in FIG. 1, the depth (or height) of the dividing notch, as measured from a root or valley 30 to ridgelines 24c or 24d, can vary from a maximum near the center of the tablet to a minimum near ends of the tablet.

Figure 6:
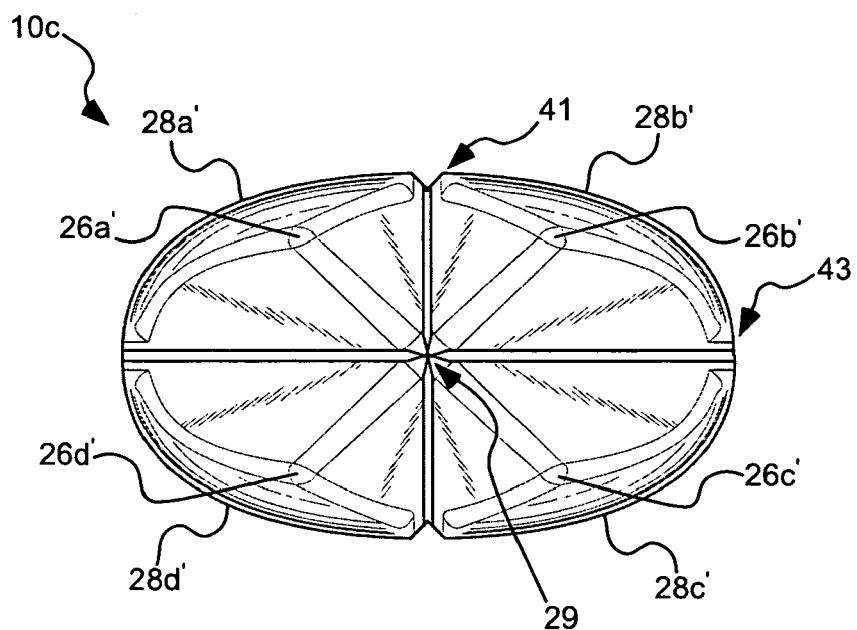
FIG. 6 is a top view of another divisible tablet in accordance with an embodiment of the invention.
Figure 7:
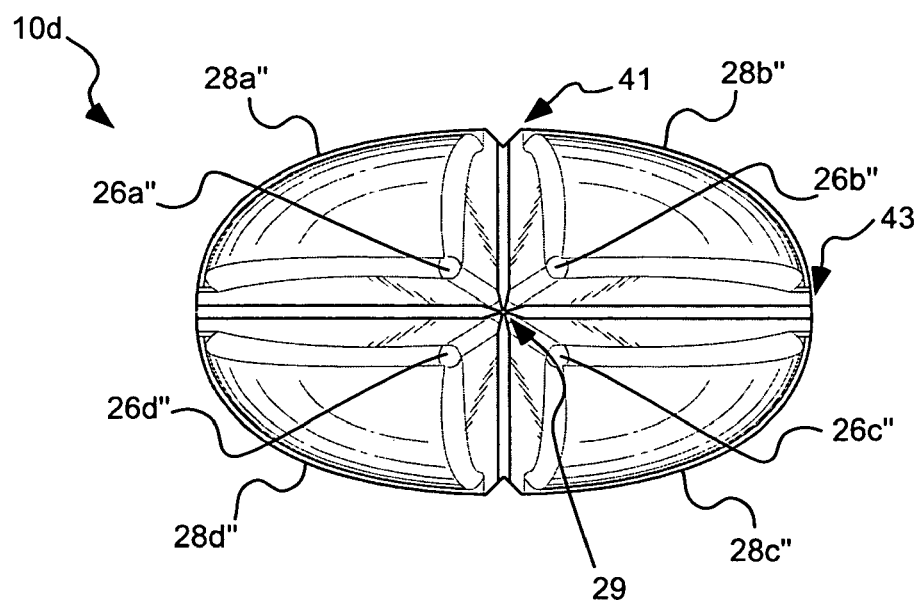
FIG. 7 is a top view of another divisible tablet in accordance with an embodiment of the invention.

As shown in FIGS. 6 and 7, the positions of the apexes adjacent the dividing notches can vary from one embodiment of the invention to another. In the examples shown in FIGS. 6 and 7, the apexes 26a', 26b', 26c' and 26d' of tablet 10c, and the apexes 26a", 26b", 26c" and 26d" of tablet 10d, are offset a lateral distance from a center 29 of the tablet, and can be offset a horizontal distance from the center of the tablet.

While the horizontal and vertical offset distances can vary, in one embodiment the lateral offset distance and the horizontal offset distance can be substantially equal, as shown for exemplary purposes in FIG. 6. In the embodiment illustrated in FIG. 6, the lateral offset distance is about 75% of a total distance from the center of the tablet to a lateral edge 41 of the tablet. The horizontal offset distance can be about 30% of a total distance from the center of the tablet to an end 43 of the tablet. In one aspect of the invention, the apex (or apexes) can be located closer to a lateral edge of the tablet than to the center of the tablet, as shown, for example in FIG. 6.

By varying the locations of the apexes while substantially maintaining the general curvature of the upper convex surfaces bordering the dividing notches, the angle or pitch of the dividing walls can be varied. In one aspect of the invention, the angle or pitch of the dividing walls can be about 45 degrees. In other aspects, the angle or pitch can vary from about 30 degrees to about 75 degrees, inclusive of angles within this range. By varying the locations of the apexes, and/or the pitch of the dividing walls, the divisible tablet can be altered to provide a desired ease of divisibility for a range of formulations.

For example, a formulation that results in a tablet having physical properties that tend to be relatively easily fractured can be provided in a tablet having relatively steeply pitched dividing notch walls, such as tablet 10*d* shown in FIG. 7. A formulation that results in a tablet having physical properties that tend to be relatively more difficult to fracture can be provided in a tablet with relatively broadly angled dividing walls, such as tablet 10*c* shown in FIG. 6. By varying the pitch or angle of the diving notch walls, the leverage a consumer is able to manually apply to the dividing notch is increased.

In one embodiment of the invention, best shown in FIGS. 1-3, the lower portion 14 of the tablet 10*a* can include a lower convex surface 14*a*. The lower convex surface can extend substantially uninterrupted across the lower portion of the tablet. In one embodiment, one or more of the convex surfaces 16*a*, 16*b*, 16*c* or 16*d* can include a curvature that, when extrapolated across the at least one dividing notch, converges into a shape substantially the same as a shape of the lower portion. Thus, the convex surfaces can include shapes that are similar to corresponding portions of the lower convex surface. One potential resulting shape of the extrapolated convex surfaces is shown by example at 36*a* in FIGS. 1 and 36*b* in FIG. 3. As will be appreciated, the extrapolated shape can be substantially similar to the shape of the opposing, lower convex surface 14*a*.

Figure 4:
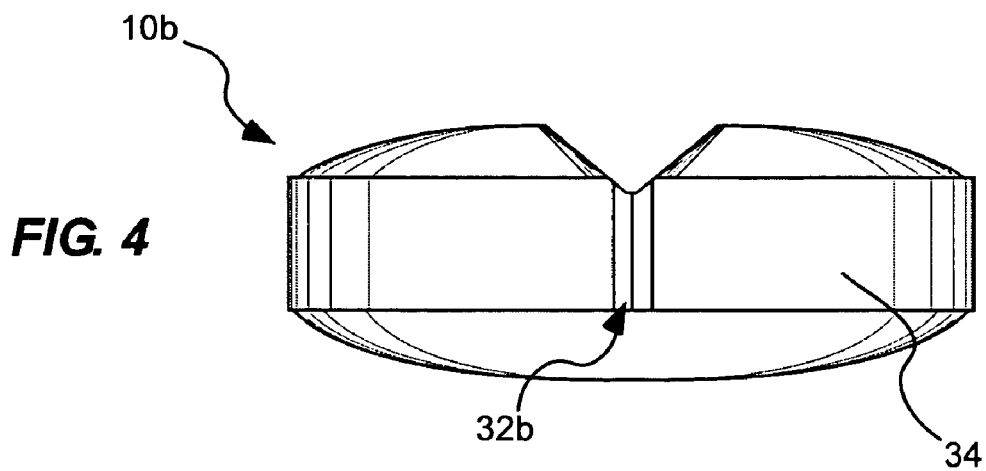
FIG. 4 is a side view of another divisible tablet in accordance with an embodiment of the present invention.
Figure 5:
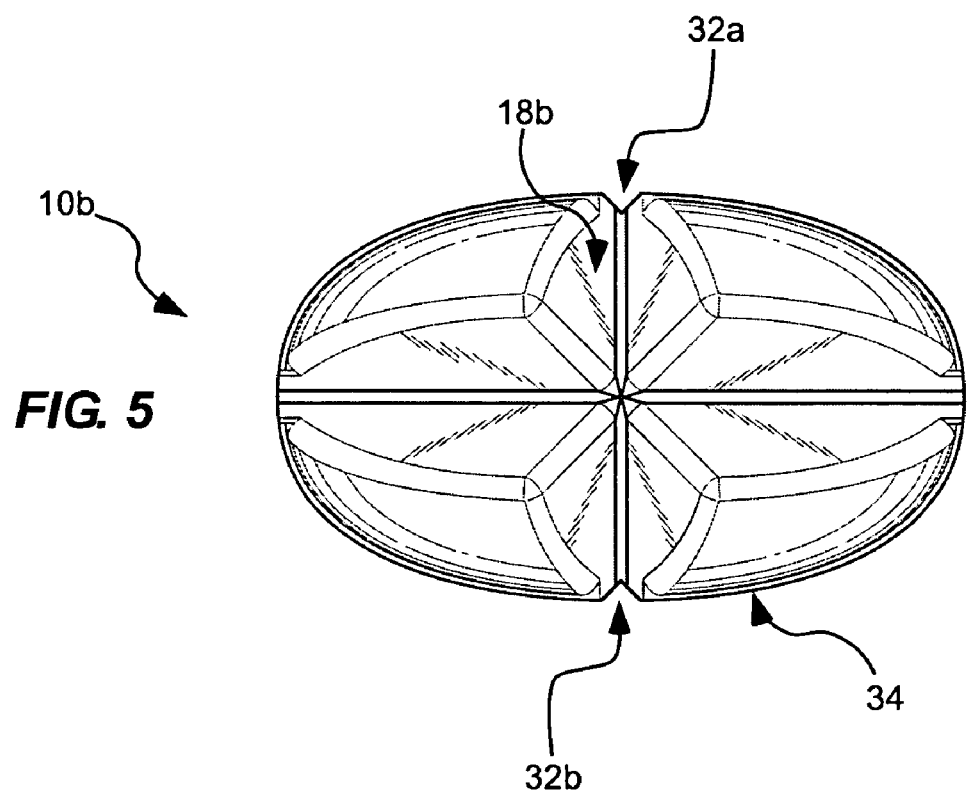
FIG. 5 is a top view of the divisible tablet of FIG. 4.

Turning now to FIGS. 4 and 5, in one aspect of the invention, at least one edge dividing notch 32*a*, 32*b* can be formed in an edge 34 of the tablet. In the embodiment shown, the edge dividing notches are formed orthogonally to the at least one dividing notch and are aligned with the laterally extending dividing notch 18*b*. The edge dividing notches can aid in accurately and easily dividing the tablet into the one or more segments or sub-portions. While the edge dividing notches illustrated in FIGS. 4 and 5 are shown formed along the lateral sides of the tablet 10*b*, it is to be understood that edge (or end) dividing notches (not shown) can be formed at lateral ends of the tablet, in addition to or instead of the edge dividing notches 32*a*, 32*b*.

While the tablets shown in the present drawings include a generally ovoid shape (as viewed from atop the tablet), in some embodiments of the invention the tablet can include a variety of other shapes, including, without limitation, generally round shapes, "caplet" shapes, polyhedral shapes (e.g., triangular, rectangular, etc.). In these and other embodiments, the configuration of the dividing notches can be selected so as to maximize the ease and accuracy with which the tablets can be divided. In particular, the location, orientation, configuration and number of dividing notches can be varied along with the shape of the tablet to provide the most effective divisible tablet for the pharmaceutical agent being delivered.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. A divisible pharmaceutical tablet, comprising:
    (a) an upper portion and a lower portion wherein the upper portion includes at least one upper convex surface bordering at least one upper dividing notch comprising two notch sides and a root, and wherein the lower portion includes at least one lower convex surface;
    (b) at least one edge dividing notch; and
    (c) a ridgeline formed between the at least one upper dividing notch and the at least one upper convex surface; the upper convex surface having an apex located along the ridgeline at a point above which no other portion of the ridgeline rises, wherein said tablet is ovoid in shape and wherein at least one of the notch sides is concave.

2. The tablet of claim 1, wherein the apex is offset at least one of: a lateral distance from a center of the tablet; or a horizontal distance from the center of the tablet.

3. The tablet of claim 2, wherein the apex is offset both a lateral distance from the center of the tablet and a horizontal distance from the center of the tablet.

4. The tablet of claim 3, wherein the lateral offset distance and the horizontal offset distance are substantially equal.

5. The tablet of claim 3, wherein the lateral offset distance is about 75% of a total distance from the center of the tablet to a lateral edge of the tablet.

6. The tablet of claim 5, wherein the horizontal offset distance is about 30% of a total distance from the center of the tablet to an end of the tablet.

7. The tablet of claim 1, wherein the apex is located closer to a lateral edge of the tablet than to a center of the tablet.

8. The tablet of claim 1, wherein the lower convex surface is a substantially continuous, uninterrupted surface.

9. The tablet of claim 1, wherein the upper dividing notch includes a varying width, with a greatest width formed adjacent a center of the upper dividing notch.

10. The tablet of claim 1, wherein the upper dividing notch includes a varying depth, with a greatest depth formed adjacent a center of the upper dividing notch.

11. The tablet of claim 1, further comprising a second upper dividing notch, the two upper dividing notches extending across the upper portion in different directions of extension.

12. The tablet of claim 11, wherein one of the upper dividing notches extends longitudinally across the tablet and wherein another of the upper dividing notches extends laterally across the tablet; a longitudinal dimension of the tablet being greater than a lateral dimension of the tablet.

13. The tablet of claim 11, wherein each of the two upper dividing notches extends across the upper portion at an oblique angle relative to a longitudinal axis of the tablet.

14. The tablet of claim 13, wherein each of the two upper dividing notches extends across the upper portion at an angle of about 45 degrees relative to the longitudinal axis of the tablet.

15. The tablet of claim 11, wherein the tablet is divisible into four segments of substantially equal volume, each of the segments including an upper section that includes three sides of differing geometry.

16. The tablet of claim 1, wherein the upper dividing notch creates a sufficient weakness in the tablet to facilitate division of the tablet by manual application of force by a consumer to portions of the tablet.

17. The tablet of claim 1, wherein the ridgeline includes rounded edges.

18. The tablet of claim 1, wherein the tablet contains levetiracetam.

19. The tablet of claim 1, wherein the tablet contains escitalopram.

20. The tablet of claim 1, wherein the tablet contains oxcarbazepine.

21. A divisible pharmaceutical tablet, comprising:
an upper portion and a lower portion, the lower portion including at least one lower convex surface; and
the upper portion including a plurality of upper convex surfaces bordered by at least one dividing notch comprising two notch sides and a root;
wherein a width of the at least one dividing notch tapers from a largest width adjacent a center of the notch to a narrowest width adjacent an edge of the tablet and wherein at least one of the notch sides is concave.

22. The tablet of claim 21, wherein a depth of the dividing notch tapers from a largest depth adjacent a center of the notch to a smallest depth adjacent an edge of the tablet.

23. The tablet of claim 21, further comprising a pair of dividing notches, the pair of dividing notches extending across the upper portion in different directions of extension.

24. The tablet of claim 23, wherein the tablet is divisible into four segments of substantially equal volume, each of the segments including an upper section that includes three sides of differing geometry.

25. The tablet of claim 23, wherein each of the dividing notches creates a sufficient weakness in the tablet to facilitate division of the tablet by manual application of force by a consumer to portions of the tablet.

26. The tablet of claim 21, further comprising at least one edge dividing notch formed in an edge of the tablet orthogonally to the at least one dividing notch.

27. The tablet of claim 21, wherein the tablet contains levetiracetam.

28. The tablet of claim 21, wherein the tablet contains escitalopram.

29. The tablet of claim 21, wherein the tablet contains oxcarbazepine.

30. A divisible pharmaceutical tablet, comprising:
an upper portion and a lower portion, the lower portion having a lower, substantially uninterrupted convex surface; and
the upper portion including a plurality of upper convex surfaces with a pair of dividing notches wherein at least one of the dividing notch comprises two notch sides and a root wherein at least one of the notch sides is concave, wherein the pair of dividing notches border at least some of the upper convex surfaces;
wherein the dividing notches extend across the upper portion in different directions of extension.

31. The tablet of claim 30, wherein ridgelines are defined between the dividing notches and the upper convex surfaces, and wherein the upper convex surfaces each have an apex located along a ridgeline at a point above which no other portion of the ridgeline rises.

32. The tablet of claim 31, wherein the ridgelines include rounded edges.

33. The tablet of claim 30, wherein one of the dividing notches extends longitudinally across the tablet and wherein another of the dividing notches extends laterally across the tablet; a longitudinal dimension of the tablet being greater than a lateral dimension of the tablet.

34. The tablet of claim 30, wherein the tablet is divisible into four segments of substantially equal volume, each of the segments including an upper section that includes three sides of differing geometry.

35. The tablet of claim 30, wherein each of the dividing notches creates a sufficient weakness in the tablet to facilitate division of the tablet by manual application of force by a consumer to portions of the tablet.

36. The tablet of claim 30, wherein the tablet contains levetiracetam.

37. The tablet of claim 30, wherein the tablet contains escitalopram.

38. The tablet of claim 30, wherein the tablet contains oxcarbazepine.

39. A divisible pharmaceutical tablet, comprising:
an upper portion and a lower portion;
the upper portion including a plurality of upper convex surfaces with at least one dividing notch separating the upper convex surfaces wherein the dividing notch comprises two notch sides and a root wherein at least one of the notch sides is concave; and
each of the upper convex surfaces having a curvature that, when extrapolated across the at least one dividing notch, converges into a shape substantially the same as a shape of the lower portion.

40. The tablet of claim 39, wherein the lower portion includes a substantially uninterrupted lower convex surface.

41. The tablet of claim 39, wherein the at least one dividing notch includes a varying width, with a greatest width formed adjacent a center of the dividing notch.

42. The tablet of claim 41, wherein the at least one dividing notch includes a varying depth, with a greatest depth formed adjacent an end of the dividing notch.

43. The tablet of claim 39, further comprising a pair of dividing notches, the pair of dividing notches extending across the upper portion in different directions of extension.

44. The tablet of claim 43, wherein one of the dividing notches extends longitudinally across the tablet and wherein another of the dividing notches extends laterally across the tablet; a longitudinal dimension of the tablet being greater than a lateral dimension of the tablet.

45. The tablet of claim 43, wherein the tablet is divisible into four segments of substantially equal volume, each of the segments including an upper section that includes three sides of differing geometry.

46. The tablet of claim 39, wherein the dividing notch creates a sufficient weakness in the tablet to facilitate division of the tablet by manual application of force by a consumer to portions of the tablet.

47. The tablet of claim 39, wherein the tablet contains levetiracetam.

48. The tablet of claim 39, wherein the tablet contains escitalopram.

49. The tablet of claim 39, wherein the tablet contains oxcarbazepine.

* * * * *